United States Patent [19]

Matsumoto et al.

[11] Patent Number: 4,753,929
[45] Date of Patent: Jun. 28, 1988

[54] FLAVONE GLYCOSIDE

[75] Inventors: Takeshi Matsumoto; Tsuyoshi Sei, both of Himeji, Japan

[73] Assignee: Daicel Chemical Industries, Ltd., Osaka, Japan

[21] Appl. No.: 24,223

[22] Filed: Mar. 10, 1987

[30] Foreign Application Priority Data

Mar. 12, 1986 [JP] Japan .................................. 61-54174
May 21, 1986 [JP] Japan ................................. 61-116714

[51] Int. Cl.⁴ ....................... A61K 31/70; C07H 17/04
[52] U.S. Cl. ............................................. 514/27; 536/8
[58] Field of Search ............................. 514/27; 536/8

[56] References Cited

U.S. PATENT DOCUMENTS 4,414,207 11/1983 Nair et al. ................................ 536/8

FOREIGN PATENT DOCUMENTS 2204986 8/1973 Fed. Rep. of Germany .......... 536/8

*Primary Examiner*—J. R. Brown
*Assistant Examiner*—Elli Peselev
*Attorney, Agent, or Firm*—Flynn, Thiel, Boutell & Tanis

[57] ABSTRACT

A flavone glycoside having the formula is isolated from the natural source and is found to be effective to amelioration of the hemolinetic disturbance.

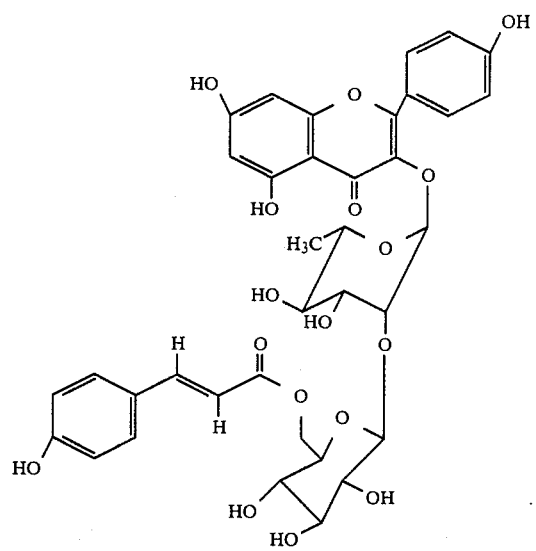

2 Claims, 1 Drawing Sheet

FLAVONE GLYCOSIDE

The present invention relates to a novel flavone glycoside useful as a medicine for the amelioration of hemokinetic disturbance.

An extract from dried leaves of ginkgo is used as a medicine for the therapy of hemokinetic disturbance of cerebral and peripheral arteries in Europe. The main components of the extract are quercetin glycoside, isoquercetin glycoside, kaempferol-3-rhamnoside glycoside, luteolin glycoside, and sitosterol glycoside, as described in Japanese Patent Publication No. 27,323/1974. More specifically, for example, kaempferol glycoside includes kaempferol-3-rhamnoglucoside having a molecular formula of $C_{27}H_{30}O_{15}$ and kaempferol-glucoside of which the heptaacetylated derivative has a molecular formula of $C_{35}H_{34}O_{18}$, as described in Arzneimitielforschung, 18, 537–53 (1968). Recently, 5,7,3',4'-tetrahydroxyflavono-3-O-α-rhamnopyranosyl-4-O-β-D-(6'''-trans-p-coumaroyl)-glucopyranoside was isolated from the extract as mentioned above [Arzteitschrift für Naturheilverfahren, 22, 593–604 (1981)].

However, the above-mentioned extract is now used without a detailed understanding of not only the pharmacological activity of each of flavone glycosides as the main components of the extract but also the composition of the extract and the contents of the components. The inventors of the present invention have made investigations to find out the effective components among flavone glycosides contained in leaves of ginkgo and the utilization of these components.

The inventors of the present invention has isolated of the flavone glycosides contained in ginkgo, compared their physical properties with those of the all flavone glycosides already isolated, and found that one of the effective components is a novel flavone glycoside. Thus, the present invention has been completed.

Specifically, the present invention provides a novel flavone glycoside represented by the following formula [I]:

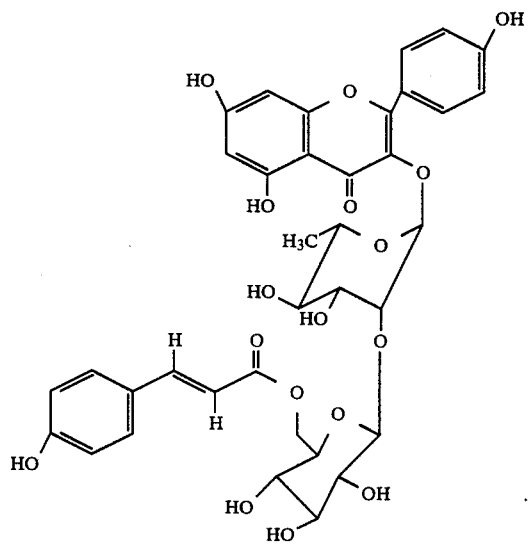

The instant invention comprises a flavone glycoside having the above mentioned formula, a pharmaceutical composition which comprises a phamacologically effective amount of said flavone glycoside and a pharmacologically acceptable carrier and a method for ameliorating the hemokinetic disturbance with administration of said flavone glycoside.

The invention further proposes a process for preparing said flavone glycoside, which comprises the steps of extracting leaves of ginkgo with a lower alcohol or a mixture of water and a lower alochol, treating the extract with a non-polar solvent to remove lipophilic compounds therefrom, then treating the resulting extract with an extraction solvent to obtain a crude fraction containing therein said flavone glycoside and subjecting said crude fraction to reversed-phase silica gel column chromatography, using a mixture of water and methanol or a mixture of water or acetonitrile for elution, in order to obtain said flavone glycoside.

The molecular formula of the compound of the present invention is $C_{36}H_{36}O_{17}$. The compound has a molecular weight of 740 and a melting point of 195° C. The compound of the present invention has the following physical properties:

(1) FD-MS: m/z 763 (M+Na)

Figure 1:
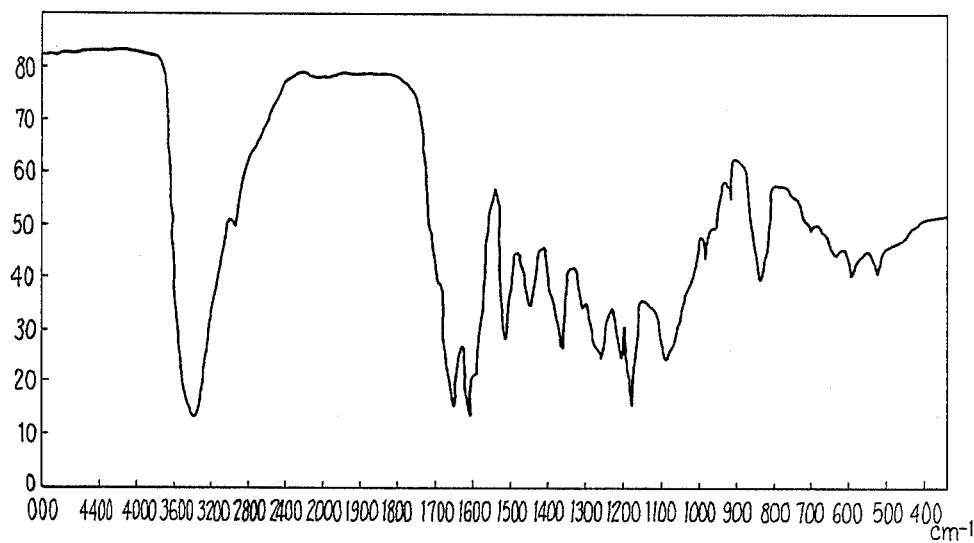
FIGS. 1, 2, and 3 are the IR stectrum, $^1$H-NMR spectrum and $^{13}$C-NMR spectrum, respectively, of the novel flavone glycoside (formula I).

(2) UV(MeOH): $\lambda_{max}$ 312 (ε: 24400), 300 (sh), 265 (ε: 19900) nm (3) IR(KBr): $\nu_{max}$ 3400, 1655, 1605, 1515, 1360, 1175, 835 cm$^{-1}$ (FIG. 1)

Figure 2:
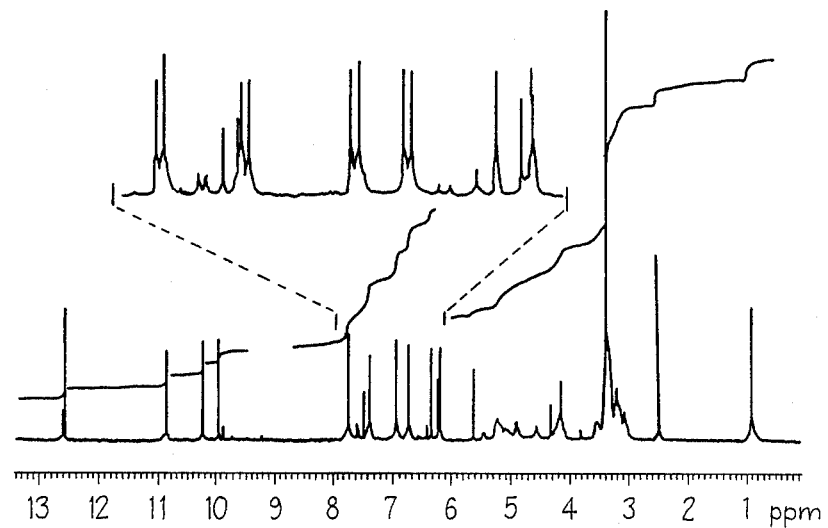

(4) $^1$H-NMR(DMSO): δ12.56(1H, s, OH-5), 10.83 (1H, s, OH-7), 10.23(1H, s, OH-4'), 9.95 (1H, s, OH-7''), 7.73(2H, d, J=8, H-2', 6'), 7.40(1H, d, J=15, H-3''), 7.38(2H, d, J=8, H-5'', 9''), 6.92(2H, d, J=8, H-3', 5'), 6.69(2H, d, J=8, H-6'', 8''), 6.32(1H, d, J=2, H-8), 6.19(1H, d, J=15, H-2''), 6.17(1H, d, J=2, H-6), 5.62(1H, brs, H-1'''), 5.3–4.5(5H, OH), 4.33(1H, d, J=8, H-1''''), 4.2–3.0(10H, —CH—O, —CH$_2$O), 2.5(3H, d, J=2, H-6''') ppm (FIG. 2)

Figure 3:
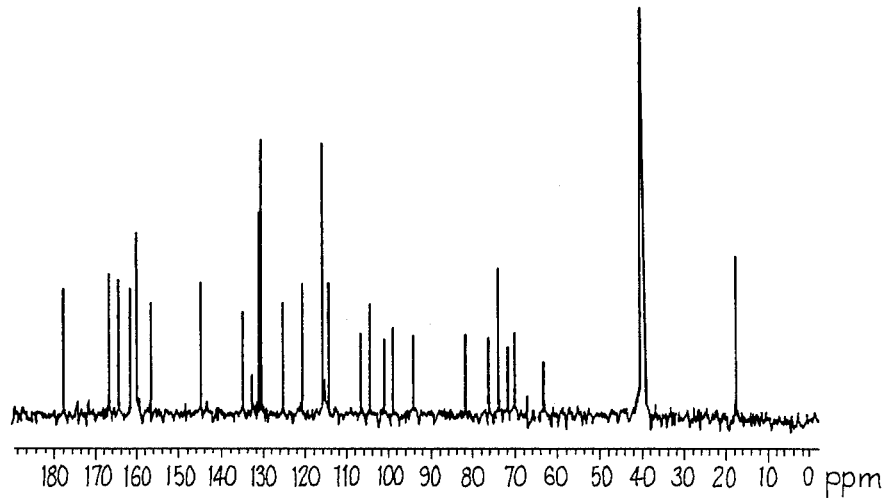

(5) $^{13}$C-NMR(DMSO): δ177.2, 165.9, 163.7, 160.9, 159.6, 159.3, 156.2, 156.0, 144.3, 134.1, 130.2(2C), 129.7(2C), 124.7, 120.1, 115.3(2C), 115.1(2C), 113.6, 105.8, 103.8, 100.4, 98.4, 93.5, 81.4, 75.9, 73.6(2C), 71.6, 70.3, 70.0, 69.6, 62.9, 17.4 (FIG. 3)

Proton signals of the sugar portion were analyzed mainly by the two-dimensional NMR method. The result of assignment of carbon signals by the selective decoupling method revealed that a carbon signal at the 2-position of rhamnose appears to be far downfield, thus proving that the bond of the sugar portion is (1→2). Accordingly, the compound [I] is kaempferol 3-O-α-(6'''-p-coumaroylglucosyl-β-1,2-rhamnoside).

The compound of the present invention can be obtained by the following method.

Leaves of ginkgo are subjected to extraction with a lower alcohol or an aqueous lower alcohol. Lipophilic compounds are removed from the obtained extract by using a non-polar solvent such as carbon tetrachloride, followed by extraction with ethyl acetate, butanol, methyl ethyl ketone, or propanol. Thus, a crude fraction containing the flavone glycoside represented by the formula [I] is obtained. This fraction is subjected to reversed-phase silica gel column chromatography in which elution is effected with a solvent mixture of methanol-water or acetonitrile-water. An eluate containing the compound of the formula [I] as the main component is concentrated to obtain a substantially pure compound [I].

In order to obtain a pure compound [I], the substantially pure compound is recrystallized from methanol-water or ethanol-water.

The novel flavone glycoside of the present invention can be used in the form of an effective composition containing the same in an amount of a non-toxic level as a medicine for amelioration of hemokinetic disturbance. It can be used in the form of a preparation suitable for peroral or parenteral administration. Peroral preparations include solid ones such as tablet, capsule, troche, granule, and powder; and liquid ones such as solution and syrup. Parenteral preparations include injection and suppository. The above-mentioned various preparations can be produced using an inorganic or organic, solid or liquid filler commonly employed according to any well-known method.

EXAMPLE 1

3 kg of dry leaves of ginkgo were heated under reflux in 20 l of methanol for 3 hours. The leaves were filtered off, and the resulting methanol solution was concentrated. The obtained extract was suspended in 2 l of water, followed by extraction with 3 l of chloroform and subsequently 4 l of ethyl acetate. 42 g of the ethyl acetate extract was subjected to a reversed-phase silica gel column ($C_{18}$). A fraction eluted with methanol-water (2:3) was concentrated to obtain 1.2 g of crystals. The obtained compound has the aforementioned physical properties. Thus, it was concluded that the compound has a structural formula represented by the formula I.

EXAMPLE 2

10 kg of dry leaves of ginkgo were heated under reflux in a solvent mixture composed of 54 l of methanol and 32 l of water for 3 hours. The leaves were filtered off, and the resulting solution was admixed with 28 l of chloroform to remove a chloroform-soluble fraction by extraction. Subsequently, the same procedure was repeated with 5 l and thereafter 2 l of chloroform. The remaining water-methanol solution was concentrated. The aqueous solution obtained by removing methanol was subjected to extraction with a solvent mixture composed of 12 l of ethyl acetate and 6 l of propanol, and subsequently with 5 l of ethyl acetate. 230 g of the concentrated product of the ethyl acetate-propanol solution was supplied to a reversed-phase silica gel column ($C_{18}$). 12 g of an extract obtained by concentrating a fraction eluted with methanol-water (1:1) was supplied again to a reversed-phase silica gel column ($C_{18}$). 6.7 g of crystals of the compound of formula I was obtained from a fraction eluted with methanol-water (2:3).

What is claimed is:

1. A substantially pure flavone glycoside having the formula:

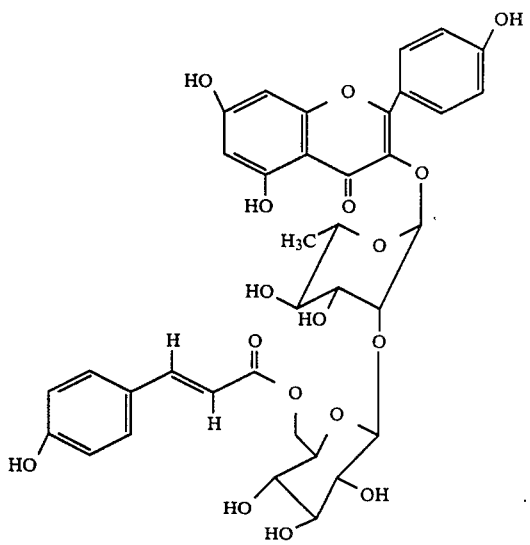

2. A pharmaceutical composition which comprises a pharmacologically effective amount of said flavone glycoside as defined in claim 1 and a pharmacologically acceptable carrier.

* * * * *